United States Patent [19]

Ono et al.

[11] Patent Number: 4,770,163
[45] Date of Patent: Sep. 13, 1988

[54] FIBERSCOPE

[75] Inventors: Kimizo Ono; Koichi Tsuno, both of Osaka, Japan

[73] Assignee: Sumitomo Electric Industries, Ltd., Osaka, Japan

[21] Appl. No.: 561,705

[22] Filed: Dec. 15, 1983

[30] Foreign Application Priority Data

Dec. 15, 1982 [JP] Japan .................. 57-219740

[51] Int. Cl.⁴ .................................. A61B 1/00
[52] U.S. Cl. ...................................... 128/6
[58] Field of Search ........................... 128/4–8

[56] References Cited

U.S. PATENT DOCUMENTS 3,773,039 11/1973 Mori et al. ................ 128/6
4,024,858 5/1977 Chikama ..................... 128/4
4,369,768 1/1983 Yukovic ..................... 128/6
4,418,688 12/1983 Loeb ......................... 128/6

FOREIGN PATENT DOCUMENTS 1248224 8/1967 Fed. Rep. of Germany .......... 128/6

Primary Examiner—Max Hindenburg
Attorney, Agent, or Firm—Sughrue, Mion, Zinn, Macpeak & Seas

[57] ABSTRACT

A fiberscope in which the cross-sectional area is maximized of a passage conveying a clear liquid through which an image of an object to be observed can be transmitted, taking into consideration constraints upon diameters of various optical fibers and a surrounding flexible tube. An image transmitting fiber is bundled together with at least one, light guiding fibers which supply illuminating light. The bundled fibers are loosely fitted within a surrounding flexible tube with a space therebetween. A cap member is provided at the end of the flexible tube and optical fiber bundle for maintaining the optical fiber bundle centered at the end of the flexible tube and for directing flows of the clear fluid around the end of the fiber bundle.

4 Claims, 2 Drawing Sheets

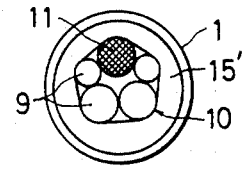
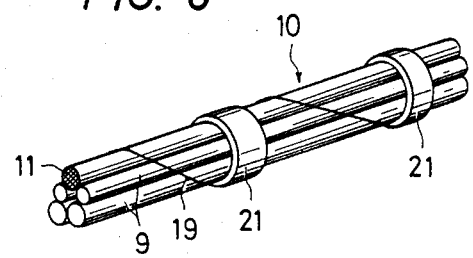
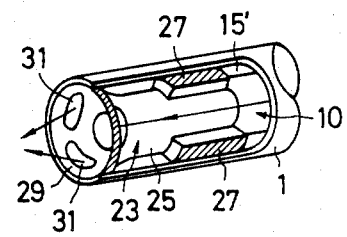
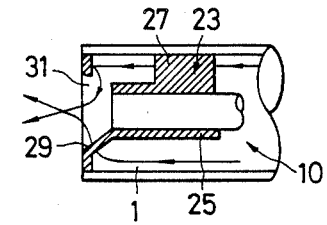

FIBERSCOPE

BACKGROUND OF THE INVENTION

The invention pertains to a fiberscope or endoscope. Specifically, the invention relates to a fiberscope which may be used for observing a desired region ordinarily obscured by an opaque fluid. Such devices may be used, for instance, for optically observing and determining the condition of regions such as blood vessels and the heart which are ordinarily filled with blood, and also for industrial applications, for instance, in a tank filled with an opaque fluid.

A prior art fiberscope of the same general type to which the invention pertains is illustrated in FIGS. 1 through 3 of the drawings. The fiberscope includes a flexible tube 1 through which pass light guiding fibers 9 for transmitting illuminating light from a light source 3 to a region 5 to be observed, here, the interior of a blood vessel 7. An image transmitting fiber 11 also passes through the flexible tube 1. At the outer end of the image transmitting fiber 11 is providing a lens for forming an image of the object being observed. A fluid guide passage 15 is also provided within the flexible tube 1. The fluid guide passage 15 is used for introducing a clear fluid to the region between the lens at the end of the image transmitting fiber 11 and the object being observed. For instance, for medical uses, normal saline is an appropriate fluid. In the case illustrated in FIG. 1, normal saline is supplied from a syringe 13. A hood 17 is provided around the outward end of the flexible tube 1, light guiding fibers 9, image transmitting fiber 11 and fluid guide passage 15.

In use, the normal saline or other clear liquid is held within the hood 17 so as to provide a transparent region between the lens at the end of the image transmitting fiber 11 and the object to be observed. In the case that blood, for instance, is continuously flowing past the object to be observed, it is necessary to supply the normal saline at a flow rate approximately the same as the flow rate of the blood, typically, about 50 cm³/sec.

As illustrated specifically by FIG. 3, in the prior art fiberscope, the liquid guide passage 15, which is cylindrical in cross section, is disposed between the inner walls of the tube 1 and the light guiding fibers 9. Due to physiologically imposed restrictions, the outer diameter of the tube 1 is limited to about 4 mm. Because of this fact, the effective cross-sectional area of the passage 15 was insufficient for introducing normal saline at a sufficient flow rate for normal blood flow rates.

As an alternative to the use of a clear solution, a transparent balloon can be blown up around the end of the fiberscope in the region to be observed. This approach, however, is not usable in many situations, particularly, in regions where it is not possible to interrupt the flow of blood because to do so would inflict injury to the patient.

It is thus a primary object of the present invention to eliminate the drawbacks of prior art fiberscopes described above.

SUMMARY OF THE INVENTION

In accordance with the above and other objects, the invention provides a fiberscope including an image transmitting fiber bundled together with light guiding fibers which transmit illuminating light to the object to be observed. A fluid guide passage for introducing transparent fluid is formed between the outside of the bundled optical fibers and the inner surface of a surrounding flexible tube. This construction provides a maximized cross-sectional area for the fluid guide passage, taking into consideration constraints upon the diameter of the flexible tube and the diameters of the optical fibers.

BRIEF DESCRIPTION OF THE DRAWINGS

FIG. 5 is a cross-sectional view of the fiberscope of FIG. 4;

FIG. 6 is a fragmentary perspective view of a fiber bundle used in the fiberscope of FIG. 4;

FIG. 7 is a fragmentary, partially cross-sectional view showing the end of the fiberscope of FIG. 1; and FIG. 8 shows a longitudinal cross-sectional view of a tip portion of a fiberscope of FIG. 4.

DESCRIPTION OF THE PREFERRED EMBODIMENTS

Figure 1:
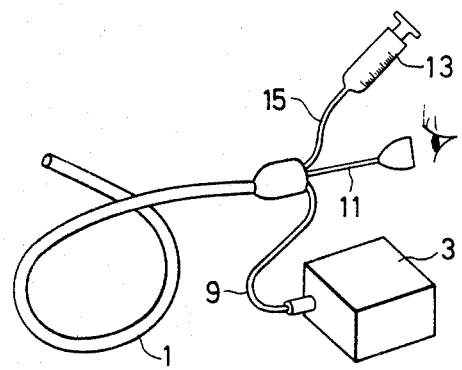
FIG. 1 is a perspective view showing an example of a conventional fiberscope.
Figure 2:
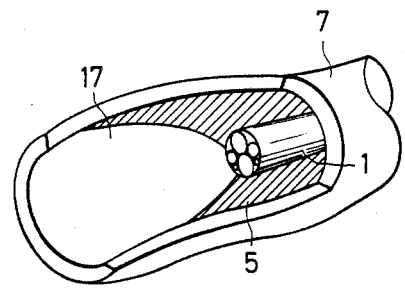
FIG. 2 is a fragmentary cross-sectional view showing an end portion of the fiberscope of FIG. 1.
Figure 3:
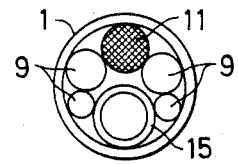
FIG. 3 is cross-sectional view of the fiberscope of FIG. 1.
Figure 4:
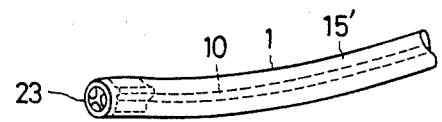
FIG. 4 is a fragmentary perspective view of a fiberscope according to the invention showing the portion thereof which is inserted in a blood vessel or other passage-way.

A fiberscope constructed in accordance with the invention is shown in FIGS. 4 through 8. Here, it is assumed that the fiberscope is applied for viewing regions within the interior of the human body through a blood vessel. As in the case of the prior art, an image transmitting fiber 11 is provided at the end of which is disposed an image-forming lens which forms an image of the object being observed. Light guiding fibers 9, as shown best in FIG. 6, are bundled together with the image transmitting fiber 11. A fluid guide passage 15', through which a solution such as normal saline may be introduced, is formed in a space between the inner wall of a flexible tube 1 and the bundle 10 of image transmitting fiber 11 and the light guiding fibers 9. The image transmitting fiber 11 and the light guiding fibers 9 are held together as a bundle 10 by a thin thread or tape 19 made of an appropriate material. The thread or tape 19 is secured by small ring-like bands 21 made of a heat shrinkable tubing material or the like. Bands 21 are spaced apart by a suitable interval, as indicated in FIG. 6.

The bundle 10 is loosely fitted within the flexible tube 1, except for the end region. At the end region, as shown best in FIGS. 7 and 8, a cap 23 is provided to maintain the bundle 10 centered within the flexible tube 1. The cap 23 includes a sleeve portion 25 which holds the tip of the bundle 10, spacer portions 27 which abut the inner surface of the tube 1 and which are circumferentially spaced from one another about the sleeve, a front wall portion 29 having a dish-like form extending forwardly of the end of the sleeve portion 25 with the outer periphery of a front wall portion 29 abutting the inner surface of the tube 1, and outlets 31 formed in the front wall portion 29 so as to provide an outlet for the normal saline or other solution introduced through the fluid guide passage 15'.

As shown best in FIG. 8, the interior of the front wall portion 29 defines a guide wall upstream of the outlet 31, thereby directing, as indicated by arrows in FIG. 8, a flow of the saline solution from the fluid guide passage 15' around the front of the fiber bundle 10. In this manner, a flow of normal saline is present at all times in the space between the lens at the end of the fiber bundle 10 and the object to be observed. Further, with the fiberscope of the invention constructed as described above, the cross-sectional area of the fluid guide passage 15' is maximized, taking into consideration the constraints upon the diameters of a flexible tube 1 and the members of the fiber bundle 10.

The geometric configuration of the cap 23 as shown in FIGS. 7 and 8 is particularly advantageous in that opposing flows of normal saline are formed forward of the lens at the end of the image transmitting fiber 11. This has the effect of maintaining the lens surface clean. Also, maximum effectiveness is made of the available flow rate of the normal saline. Further, by forming the bands 21 of a suitable material, the fiber bundle 10 can easily be fitted through the flexible tube 1, thereby simplifying the cleaning and sterilization of the instrument.

While the preferred embodiment of the invention discussed above has been described with reference to an intravascular observation fiberscope angioscope, the invention is by no means limited thereto. That is, the fiberscope of the invention can be applied to biological observation of other organs, and also to industrial applications, for instance, for observing the interior of a tank filled with an opaque fluid. The clear solution supplied to the passage 15' should, of course, be selected in accordance with the particular application at hand.

We claim:

1. A fiberscope comprising: an image transmitting optical fiber (11), having at one end an optical system, for forming and transmitting an image of an object to be observed; at least one light guiding optical fiber (9) for transmitting illuminating light; means (19, 21) for bundling said image transmitting fiber with said at least one light guiding fiber to form a bundle (10) of optical fibers including said image transmitting fiber and said at least one light guiding fiber; a flexible tube (1), the bundled optical fibers being loosely fitted through most of the length of said flexible tube; and cap means (23) located at an outer end of said flexible tube adjacent said end of said image transmitting fiber and an end of said light guiding optical fiber for maintaining the bundled optical fibers substantially at a center of said flexible tube at said end of said flexible tube and for directing a flow of a fluid passing through a space (15') between an inner surface of said flexible tube and said bundled fibers in front of said ends of said optical fibers, wherein said cap means comprises a sleeve portion (25) in contact with said bundled optical fibers at a position behind said ends of said optical fibers, at least one spacer portion (27) extending between said sleeve portion and said inner surface of said flexible tube, and a dish-shaped front wall portion (29) having an outer periphery in contact with said inner surface of said flexible tube forward of said end of said optical fibers, at least one aperture (31) being formed in said front wall portion for directing said flow of said fluid in front of said end of said bundle.

2. The fiberscope of claim 1, wherein a plurality of said apertures are formed in said front wall portion for directing opposing flows of said fluid in front of said ends of said optical fibers.

3. The fiberscope of claim 2, wherein said bundling means comprises a thin member wrapped spirally around said bundle and a plurality of spaced bands around said bundle at predetermined intervals.

4. The fiberscope of claim 3, wherein said bands are formed of a heat shrinkable material.

* * * * *